United States Patent [19]
Earle

[11] Patent Number: 5,514,135
[45] Date of Patent: May 7, 1996

[54] BONE CEMENT DELIVERY GUN

[76] Inventor: Michael L. Earle, 279 Old Ranch Rd., Sierra Madre, Calif. 91024

[21] Appl. No.: 479,571

[22] Filed: Jun. 7, 1995

Related U.S. Application Data

[63] Continuation of Ser. No. 88,215, Jul. 6, 1993, abandoned.

[51] Int. Cl.[6] .................... B67D 5/42; A61F 200
[52] U.S. Cl. ................ 606/93; 222/389; 222/391
[58] Field of Search ............... 606/92–95; 604/57–59, 604/140–141, 143, 147; 222/388, 389, 391, 323–324, 326

[56] References Cited

U.S. PATENT DOCUMENTS

| | | | |
|---|---|---|---|
| 2,446,501 | 8/1948 | Weber | 222/389 |
| 2,818,999 | 1/1958 | Miller | 222/389 |
| 3,561,433 | 2/1971 | Kovach | 604/140 |
| 3,768,472 | 10/1973 | Hodash et al. | 222/389 |
| 4,274,163 | 6/1981 | Malcom et al. | 606/94 |
| 4,386,717 | 6/1983 | Koob | 222/389 |
| 4,441,629 | 4/1984 | Mackal | 222/389 |
| 4,595,006 | 6/1986 | Burke et al. | 606/94 |
| 4,627,434 | 12/1986 | Murray | 606/94 |
| 4,634,027 | 1/1987 | Kanarvogel | 222/389 |
| 5,181,636 | 1/1993 | Anderson et al. | 222/389 |

FOREIGN PATENT DOCUMENTS

| | | | |
|---|---|---|---|
| 1791094 | 2/1978 | Germany | 604/141 |
| 3425566 | 1/1986 | Germany | 606/94 |
| 3515101 | 10/1986 | Germany | 222/389 |

*Primary Examiner*—Stephen C. Pellegrino
*Assistant Examiner*—Nancy Mulcare
*Attorney, Agent, or Firm*—Christie, Parker & Hale

[57] ABSTRACT

A bone cement delivery gun for use in attachment of prosthetics and method of using the delivery gun. The gun comprises a reservoir and a trigger mechanism. The reservoir comprises a plunger at a first end of the reservoir and a screw mount fitting at a second end of the reservoir. The trigger mechanism comprises a first position wherein gas, from a compressed gas source, is prevented from reaching the plunger and a second position wherein compressed gas is conveyed from the compressed gas source to the plunger to thereby move the plunger in a direction toward the screw mount fitting.

10 Claims, 2 Drawing Sheets

BONE CEMENT DELIVERY GUN

CROSS-REFERENCE TO RELATED APPLICATION

This is a continuation of application Ser. No. 08/088,215, filed Jul. 6, 1993, now abandoned.

FIELD OF THE INVENTION

This invention relates to delivery of bone cement for use in surgical procedures such as hip replacements.

BACKGROUND OF THE INVENTION

Damage to the joints of the human body, due to arthritis, other degenerative diseases or trauma, often results in the need to replace the joint with a prosthetic device. In the case of hip replacement surgery, such devices include a cup which fits into the hip, and replaces the acetabulum, and a ball attached to a stem which fits into the femur and replaces the head of the femur. A cement is used to secure the prosthetic devices to the bone.

Currently, the cement used for such replacement is polymethylmethacrylate (PMMA), which requires the use of a catalyst for hardening of the cement. The catalyst, which is supplied in liquid form, must be mixed thoroughly with the methylmethacrylate monomer, and other dry components, to ensure a complete and even hardening of the cement. Typically, mixing of the components for between 0.5 to 2 minutes is required to obtain adequate mixing of the cement. After mixing, the cement is usually transferred to a delivery gun so that it can be applied to the areas required.

The time required for the cement to harden to a firm consistency is approximately 12–14 minutes, with complete hardening of the cement in about 24 hours. From the time the catalyst is mixed with the monomer the mixture begins to increase in viscosity until it eventually hardens. If there is a delay from the time the cement is mixed to the time it is delivered, as is common during a surgical procedure, the cement can become so viscous that it is very difficult or impossible to force from the delivery gun.

Currently, delivery guns are available that use a ratchet type mechanism for delivering the cement. These delivery guns are similar to that of a caulking gun for delivery of caulk to grout tiles. This ratchet type mechanism requires a great deal of strength to advance the ratchet to deliver viscous cement. Eventually the viscosity of the cement can become so great that delivery is not possible and the cement has to be discarded, necessitating the mixing of a new batch of cement. The need to mix a new batch of cement increases the length of the surgery. Also, most currently available delivery guns include metal parts and reusable components which must be cleaned and sterilized between uses.

It is desirable that a delivery gun is provided which is capable of delivering cement even when it has a high viscosity. It is also desirable that the delivery gun is disposable to minimize the clean-up required after a surgical procedure.

SUMMARY OF THE INVENTION

A bone cement delivery gun for use in attachment of prosthetics and method for using the delivery gun are described. The gun comprises a reservoir and a trigger mechanism.

The reservoir comprises a plunger at a first end of the reservoir and a screw mount fitting at a second end of the reservoir wherein the plunger pushes cement contained in the reservoir through the screw mount fitting for delivery to a patient.

The trigger mechanism comprises a first position wherein gas, from a compressed gas source, is prevented from reaching the plunger and a second position wherein compressed gas is conveyed from the compressed gas source to the plunger to thereby move the plunger in a direction toward the screw mount fitting. Pressing and releasing the trigger a few times results in a slow flow of the cement from the delivery gun whereas pushing the trigger many times results in a fast flow of the cement.

BRIEF DESCRIPTION OF THE DRAWINGS

Features, aspects and advantages of the invention will be more fully understood when considered with respect to the following detailed description, appended claims and accompanying drawings where:

DETAILED DESCRIPTION

Figure 1:
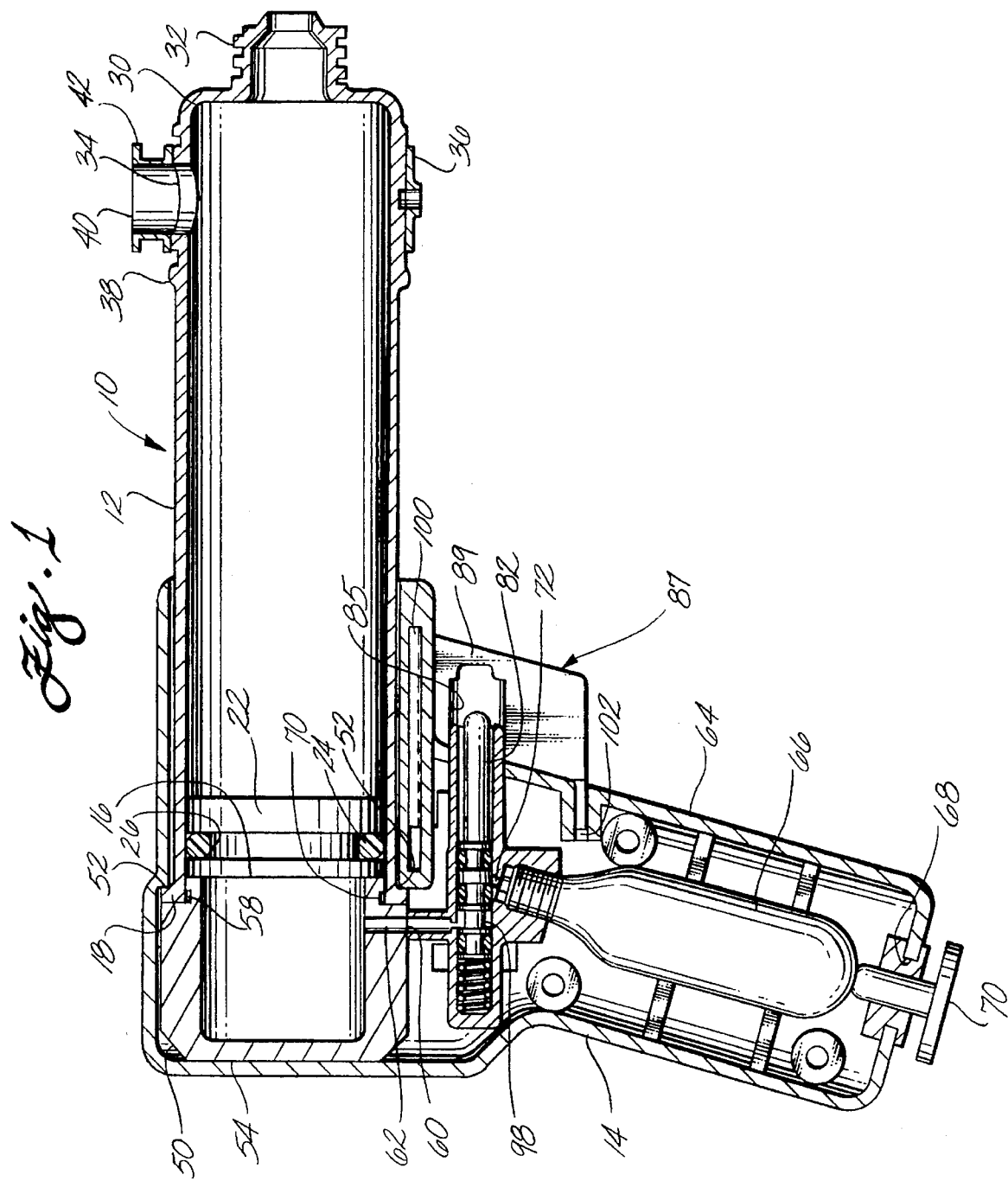
FIG. 1 is a side view, partly in section, of a bone cement delivery gun.

The present invention relates to a bone cement delivery gun 10 (see FIG. 1). The bone cement delivery gun of the present invention has the advantage of being powered by pressurized gas to facilitate delivery of bone cement to a patient.

All the components of the bone cement delivery gun are disposable. The individual components of the bone cement delivery gun are described in detail below.

In general, the bone cement delivery gun of the present invention comprises a first housing 12 and a second housing 14.

The first housing defines a cylindrically shaped bone cement reservoir. At a first end of the reservoir is an end wall 30 from which a screw mount fitting 32 extends outwardly. The screw mount fitting includes a screw thread for the attachment of extension nozzles. Extension nozzles facilitate the delivery of cement to the bone surface. Some extension nozzles are long, such as those for the delivery of cement deep into the femur. Others have relatively short nozzles for delivery to bone which is more accessible. Other nozzles may have fluted ends such as those for delivery of the cement to the acetabulum. The nozzles may also be bent or angled to facilitate the delivery of the cement to the desired site.

Located in the cylindrical wall of the reservoir is a filling port 34. In one embodiment of the present invention the filling port is located adjacent to the screw mount fitting. The filling port is used to allow mixed bone cement to flow into the reservoir for subsequent delivery to a patient.

A sleeve 36 is located around the circumference of the reservoir and is held in place by guides 38 which circumvent the outer diameter of the reservoir. The sleeve comprises a ring with an aperture 40, which is aligned with the filling port when the reservoir is to be filled. After filling the reservoir, the sleeve is rotated to move aperture 40 away from the filling port to seal the reservoir. In one embodiment of the present invention the sleeve includes a flange 42 around the circumference of aperture 40 for attaching the reservoir to the cement delivery port of a bone mixer device.

A second end 16 of the reservoir, is open. Around the edge of the open end of the reservoir is a rim 18 which extends perpendicular to the cylindrical wall to form an outwardly extending lip around the exterior of the open end of the reservoir. Rim 18 mates with shoulder 52 located on the interior of the second housing and thereby holds the first housing in place within the second housing.

Located inside the reservoir is a disc shaped plunger 22. The plunger is dimensioned so that its exterior diameter is slightly smaller than the interior diameter of the reservoir. An O-ring 24 is located in a groove 26 around the exterior of the plunger so that when the plunger is inserted into the reservoir it forms an "air tight" seal against the interior wall of the reservoir.

Attached to the open end of the reservoir, and located in the second housing, is a pressure chamber 50. The pressure chamber, in one embodiment, is made from anodized aluminum. In a preferred embodiment the pressure chamber is made from a high density plastic such as nylon, polyethylene or other suitable material. The pressure chamber is cylindrically shaped, with one end 54 of the cylinder closed and the other end 56 open. Around the exterior perimeter of the open end is a groove 58 which about rim 18 of the first housing, to hold the pressure chamber in place.

The pressure chamber includes a channel 62, which aligns with a channel 60 in the second housing. Channel 60 is made from a metal such as stainless steel and transports gas, under pressure, from the handle section 64 of the second housing to the pressure chamber. At one of its ends channel 60 connects to the pressure chamber through channel 62. At its other end it connects to a gas flow regulator 80, which is discussed in detail below.

The handle section encases a carbon dioxide ($CO_2$) cylinder 66. The $CO_2$ cylinder is placed in the handle through an access port 68 at the bottom of the handle. Once inserted into the handle the cylinder is held in place by plug 70 which is screwed into place to secure the $CO_2$ cylinder and to force the mouth of the cylinder onto a piercing element 72 (see FIGS. 2 and 3). The piercing element comprises a stainless steel hollow needle attached to the gas flow regulator. Once the cylinder mouth is pierced, the piercing element also acts as a channel to direct gas from the gas cylinder to the gas flow regulator. $CO_2$ cylinders are commercially available from Leland Limited, Inc. Bedminster N.J. Typically such cylinders are about 1.9 cm in diameter and about 6.4 cm in length and are pressurized to about 800 psi.

Figure 2:
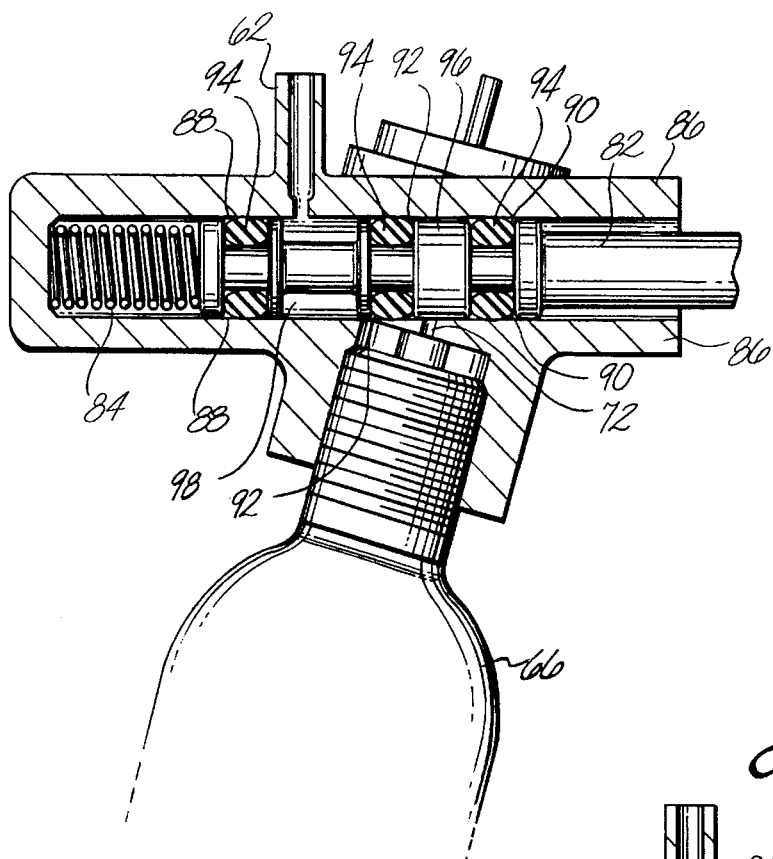
FIG. 2 is a side view, partly in section, of a gas delivery mechanism of the delivery gun of FIG. 1, in an "open" position.
Figure 3:
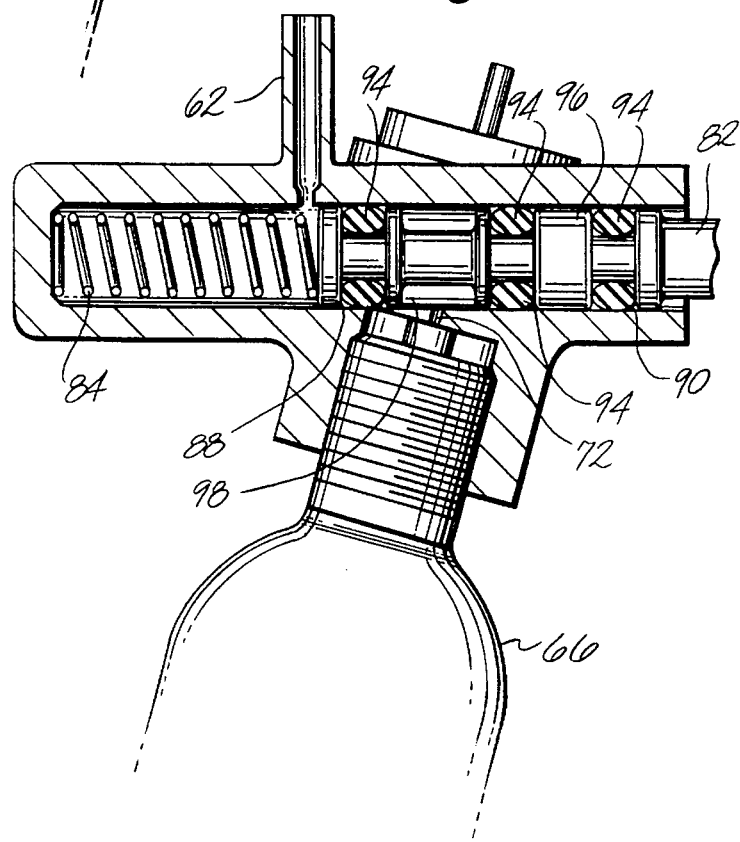
FIG. 3 is a side view, partly in section, of a gas delivery mechanism of the delivery gun of FIG. 1, in a "closed" position.

The gas flow regulator 80 comprises a shaft 82 and spring 84 (see FIGS. 2 and 3). The spring and shaft are enclosed in a generally cylindrically shaped housing 86 which is open at one end and closed at the other. The spring is placed in the cylindrical housing to abut the closed end. The shaft is then placed in the housing to abut the spring. The open end allows a trigger 87 to be pushed against the shaft, as is described in detail below.

Shaft 82 is generally cylindrical in shape with at least three indents around the circumference of the shaft. A first indent 88 and a second indent 90 are located at each end of the shaft. A third indent 92 is located approximately midway between the first and second indents. The indents are dimensioned to each seat an O-ring 94 which, when the shaft is inserted into the cylindrical housing, create an "air tight" seal against the interior wall of the housing and the shaft. Between second indent 90 and third indent 92, the diameter of the shaft is such that it is only slightly smaller than the internal diameter of the housing and forms a stopper section 96. Between the first indent 88 and third indent 92 the diameter of the shaft is smaller than the interior diameter of the housing so that when the shaft is placed in the housing an "air" space 98 is created between the interior wall of the housing and the shaft. Sections 96 and 98 are isolated from each other, and from the environment beyond the shaft, by O-rings 94.

Trigger mechanism 87 includes a slidable element 89 which is mounted in guides 100 and 102. The guides comprise a slot into which fit wings which extend perpendicularly from the slidable element of the trigger mechanism. A "cut-out" section 85 which mates with the end of shaft 82 extending out of housing 86 is included in the slidable element.

In operation, slidable element 89 is depressed to engage shaft 82. The shaft then moves against and compresses spring 84 and air space 98 is moved to align with channel 62, i.e. the open position (see FIG. 2). Gas accumulated in the air space is free to flow from the air space, through channel 62 and into chamber 50. When the shaft is in the open position the stopper section 96 is aligned with the outlet of the cylinder, blocking gas flow from the cylinder. Gas released from the air space moves through channel 60 into pressure chamber 50 where it pushes against plunger 22 into the cement reservoir. The gas pressure causes the plunger to move through the reservoir, pushing cement contained in the reservoir toward and through the screw mount fitting. Once the gas is vented from the air space the trigger is released which allows the spring to expand and thus push the shaft to the closed position.

In the closed position (see FIG. 3), when the trigger is not depressed, the air space 98 is positioned over the piercing element 72 of the cylinder and $CO_2$ gas is able to escape into and fill air space 98. The O-rings prevent the $CO_2$ from escaping from the air space. When the trigger is depressed, the shaft is again pushed against the spring and the air space is aligned with channel 62.

The cycle is then repeated as many times as may be desired to deliver the required amount of bone cement to the patient. This delivery system gives intermittent bursts of gas which can be used to deliver a constant stream of bone cement. If a slow stream is desired the trigger is pushed in and out only a few times in a given time period. If a fast stream is desired the trigger is pushed in and out a large number of times in a given time period to increase the pressure of gas in the pressure chamber to the desired level and thereby move the plunger and cement at the desired rate of flow.

In a preferred embodiment of the present invention the delivery gun is constructed from high density polyethylene, unless otherwise indicated. Polyethylene is relatively inexpensive so that the delivery gun can be disposed of after use.

After delivery of the cement to the bone, particularly in the case of delivery into the femur, it is desirable to apply pressure to the cement within the femur to ensure a "good" contact of the cement with the bone and to eliminate any air pockets which may be trapped within the cavity. In a preferred embodiment of the present invention, the delivery gun also includes a means of attaching the gun to the femur or bone. The means of attachment is designed to hold the gun against the bone so that additional pressure can be applied by pressing the trigger of the gun to force gas from the cylinder and to transfer this gas pressure into the cement filled cavity. The means of attachment prevents the delivery gun from being "pushed away" from the bone as the pressure is applied. In one embodiment the means of attachment is a ring, attached to the delivery gun which is attached over the lesser trochanter of the femur to hold the delivery gun securely in place against the femur.

The above descriptions of exemplary embodiments of a bone cement delivery gun are for illustrative purposes. Variations will be apparent to those skilled in the art, therefore, the present invention is not intended to be limited to the particular embodiments described above. The present invention may also be practiced in the absence of any element not specifically disclosed. The scope of the invention is defined by the following claims.

What is claimed is:

1. A bone cement delivery gun for use in attachment of prosthetics, the gun comprising:

a handle;

a housing attached to the handle;

a reservoir, within the housing, comprising a first end and a second end wherein a plunger is located at the first end of the reservoir and an outlet is located at the second end of the reservoir;

a cylinder, within the handle containing a compressed gas;

means for conducting gas from the cylinder to the plunger whereby the gas does not flow directly from the cylinder into the reservoir to move the plunger;

a trigger mechanism, within the handle;

a gas flow regulator in the means for conducting gas, actuated by the trigger mechanism and movable between:

a first position where a fixed volume space within the regulator is aligned with an outlet from the cylinder thereby allowing compressed gas to fill the space, but where the space is not aligned with an inlet leading to the reservoir thereby preventing gas flow to the reservoir;

a second intermediate position wherein the compressed gas, located within the regulator's fixed volume space is isolated from both the outlet from the cylinder and the inlet to the reservoir whereby the compressed gas in the cylinder can no longer flow into the regulator's fixed volume space and the compressed gas located in the regulator's fixed volume space cannot flow into the reservoir;

a third position wherein the compressed gas contained in the regulator's fixed volume space is aligned with the inlet to the reservoir allowing the compressed gas from the space to flow into the reservoir, but where the space is not aligned with the outlet from the cylinder thereby preventing gas flow from the cylinder to both the reservoir and the regulator's fixed volume space.

2. A bone cement delivery gun as recited in claim 1 wherein the compressed gas is carbon dioxide.

3. A bone cement delivery gun as recited in claim 1 wherein the reservoir further comprises a port for filling the reservoir with bone cement.

4. A bone cement delivery gun as recited in claim 1 further comprising means to connect the gun to a bone cement mixer to facilitate filling of the reservoir with bone cement.

5. In a bone cement delivery gun having a reservoir, bone cement contained in the reservoir and a trigger mechanism for initiating delivery of the cement from the reservoir to a patient wherein the improvement comprises means for delivering the cement using compressed gas which applies pressure to the plunger to thereby deliver cement from the reservoir, the delivering means having a gas flow regulator connected to the trigger mechanism that does not allow the compressed gas to flow directly from a source of compressed gas into the reservoir, wherein the gas flow regulator is movable between:

a first position where a fixed volume space within the regulator is aligned with an outlet from the gas source thereby allowing compressed gas to fill the space, but where the space is not aligned with an inlet leading to the reservoir thereby preventing gas flow to the reservoir;

a second intermediate position wherein the compressed gas, located within the regulator's fixed volume space is isolated from both the outlet from the gas source and the inlet to the reservoir whereby the compressed gas from the gas source can no longer flow into the regulator's fixed volume space and the compressed gas located in the regulator's fixed volume space cannot flow into the reservoir;

a third position wherein the compressed gas contained in the regulator's fixed volume space is aligned with the inlet to the reservoir allowing the compressed gas from the space to flow into the reservoir, but where the space is not aligned with the outlet from the gas source thereby preventing gas flow from the gas source to both the reservoir and the regulator's fixed volume space.

6. In a bone cement delivery gun as recited in claim 5 wherein the compressed gas is carbon dioxide.

7. In a bone cement delivery gun as recited in claim 5 wherein the improvement further comprises means to connect the gun to a bone cement mixer to facilitate filling of the reservoir with bone cement.

8. A method for delivering bone cement comprising the steps of:

positioning a compressed gas cylinder within a handle of a bone cement delivery gun;

filling a reservoir, comprising a first end and a second end wherein a plunger is located at the first end of the reservoir and an outlet is located at the second end of the reservoir, with bone cement;

positioning the reservoir within a housing attached to the handle of the bone cement delivery gun;

applying intermittent gas pressure, from the compressed gas cylinder to the plunger at a side opposite the second end of the reservoir, via a gas flow regulator, to thereby apply pressure to the bone cement in the reservoir such that the cement is forced through a nozzle attached to the outlet at the second end of the reservoir wherein the gas flow regulator is movable between:

a first position where a fixed volume space within the regulator is aligned with an outlet from the cylinder thereby allowing compressed gas to fill the space, but where the space is not aligned with an inlet leading to the reservoir thereby preventing gas flow to the reservoir;

a second intermediate position wherein the compressed gas, located within the regulator's fixed volume space is isolated from both the outlet from the cylinder and the inlet to the reservoir whereby the compressed gas in the cylinder can no longer flow into the regulator's fixed volume space and the compressed gas located in the regulator's fixed volume space cannot flow into the reservoir;

a third position wherein the compressed gas contained in the regulator's fixed volume space is aligned with the inlet to the reservoir allowing the compressed gas from the space to flow into the reservoir, but where the space is not aligned with the outlet from the cylinder thereby preventing gas flow from the cylinder to both the reservoir and the regulator's fixed volume space.

9. A method as recited in claim 8 wherein the gas is carbon dioxide.

10. A method as recited in claim 8 wherein the reservoir is filled by connecting it directly to a bone cement mixer.

* * * * *